(12) United States Patent
Scaglione et al.

(10) Patent No.: US 11,951,199 B1
(45) Date of Patent: Apr. 9, 2024

(54) PERSONAL SKINCARE PRODUCT

(71) Applicant: Rivercrest, LLC, Tampa, FL (US)

(72) Inventors: Anthony J. Scaglione, Tampa, FL (US); John M. Cronan, Brandon, FL (US); Juan Cobos, Brandon, FL (US)

(73) Assignee: Rivercrest, LLC

( * ) Notice: Subject to any disclaimer, the term of this patent is extended or adjusted under 35 U.S.C. 154(b) by 0 days.

(21) Appl. No.: 17/409,846

(22) Filed: Aug. 24, 2021

Related U.S. Application Data

(60) Provisional application No. 63/069,893, filed on Aug. 25, 2020.

(51) Int. Cl.
| | | |
|---|---|---|
| *A61K 8/41* | (2006.01) | |
| *A61K 8/34* | (2006.01) | |
| *A61K 8/368* | (2006.01) | |
| *A61K 8/65* | (2006.01) | |
| *A61K 8/67* | (2006.01) | |
| *A61K 8/92* | (2006.01) | |
| *A61K 8/9789* | (2017.01) | |
| *A61K 8/9794* | (2017.01) | |
| *A61K 31/14* | (2006.01) | |
| *A61K 31/355* | (2006.01) | |
| *A61K 36/185* | (2006.01) | |
| *A61K 36/63* | (2006.01) | |
| *A61K 36/886* | (2006.01) | |
| *A61K 47/10* | (2017.01) | |
| *A61K 47/12* | (2006.01) | |
| *A61K 47/42* | (2017.01) | |
| *A61K 47/44* | (2017.01) | |
| *A61K 47/46* | (2006.01) | |
| *A61Q 19/00* | (2006.01) | |

(52) U.S. Cl.
CPC .............. *A61K 8/416* (2013.01); *A61K 8/34* (2013.01); *A61K 8/345* (2013.01); *A61K 8/368* (2013.01); *A61K 8/65* (2013.01); *A61K 8/678* (2013.01); *A61K 8/92* (2013.01); *A61K 8/925* (2013.01); *A61K 8/9789* (2017.08); *A61K 8/9794* (2017.08); *A61K 31/14* (2013.01); *A61K 31/355* (2013.01); *A61K 36/185* (2013.01); *A61K 36/63* (2013.01); *A61K 36/886* (2013.01); *A61K 47/10* (2013.01); *A61K 47/12* (2013.01); *A61K 47/42* (2013.01); *A61K 47/44* (2013.01); *A61K 47/46* (2013.01); *A61Q 19/005* (2013.01); *A61K 2800/48* (2013.01)

(58) Field of Classification Search
None
See application file for complete search history.

(56) References Cited

U.S. PATENT DOCUMENTS

| | | |
|---|---|---|
| 5,143,717 A | 9/1992 | Davis |
| 2003/0194446 A1 | 10/2003 | Akes |
| 2008/0206155 A1 | 8/2008 | Tamarkin |
| 2009/0162443 A1* | 6/2009 | Anthony .............. A61K 8/8117 424/59 |
| 2015/0157583 A1 | 6/2015 | Bennett |
| 2017/0136086 A1 | 5/2017 | Chacon et al. |
| 2018/0008711 A1 | 1/2018 | Selner |
| 2019/0038750 A1 | 2/2019 | Selner |

FOREIGN PATENT DOCUMENTS

| | | | |
|---|---|---|---|
| JP | 2003176219 | * | 6/2003 |
| WO | 2004022034 A1 | | 3/2004 |

* cited by examiner

*Primary Examiner* — Michael V Meller
(74) *Attorney, Agent, or Firm* — GrayRobinson, P.A.

(57) ABSTRACT

A personal skincare product that provides cleansing, antiseptic, antibacterial, soothing, moisturizing, protective, and healing benefits to irritated skin and wounds for all ages, particularly for consumers with sensitive and fragile skin like children and the elderly. The personal skincare product comprises a topical antiseptic comprising water, benzalkonium chloride, phenoxyethanol, aloe, liquid coconut, propylene glycol, collagen, polyethylene glycol, sodium benzoate, petrolatum, lanolin, mineral oil, cod liver oil, paraffin, sodium, olive oil, cottonseed oil, vitamin E, and a non-ionic copolymer such as Poloxamer 188 or a combination therefrom.

4 Claims, No Drawings

PERSONAL SKINCARE PRODUCT

CROSS-REFERENCE TO RELATED INVENTIONS

This application claims the benefit of earlier-filed provisional application No. 63/069,893, titled "Personal Skincare Product," filed Aug. 25, 2020, the disclosure of which is hereby incorporated by reference herein.

TECHNICAL FIELD

This disclosure relates to a personal skincare product. Specifically, this disclosure relates to a foamed topical antiseptic comprising a number of ingredients having antiseptic, moisturizing, fragrance, and thickening properties distinguishing it from products currently available.

BACKGROUND OF THE INVENTION

Irritated or sensitive skin is a common problem for people of all ages and backgrounds. Likewise, small wounds such as cuts, burns, and scrapes are common. Skin may also become irritated or sensitive due to issues such as diaper rash or circumcision. It is prevalent in the industry to use products that are inconvenient and costly as well as leave either a bad smell or an oily residue. It is therefore needed to provide a product that cleanses, soothes, and protects skin that solves these problems.

Therefore, it is an object of this invention to provide an improvement which overcomes the aforementioned inadequacies of the prior art and provides an improvement which is a significant contribution to the advancement of the topical antiseptic art.

A further object of the present invention is to cleanse skin to promote comfort and healing.

A further object of the present invention is to soothe skin to promote comfort and healing.

A further object of the present invention is to add a protective barrier to skin in order to promote comfort and healing.

A further object of the present invention is to provide a topical antiseptic product that is foamed and then applied to the applicable area.

A further object of the present invention is to provide a foamed, non-aerosol topical antiseptic that provides a barrier to bacteria and other harmful substances from entering a cut or wound.

A further object of the present invention is to allow for reproducibility of testing.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, this invention comprises a topical antiseptic comprising water, benzalkonium chloride, phenoxyethanol, aloe, liquid coconut, propylene glycol, collagen, polyethylene glycol, sodium benzoate, petrolatum, lanolin, mineral oil, cod liver oil, paraffin, sodium, olive oil, cottonseed oil, vitamin E, and a non-ionic copolymer such as Poloxamer 188 or a combination therefrom.

Embodiments of the present invention are herein described by way of example and are directed to a foamed topical antiseptic. The aforementioned state of the art of topical antiseptics shows the need for improvements, specifically in the ability of the antiseptic to provide thickening agents that better bind the antiseptic to the skin and leave a lasting scent.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION

The present invention relates to a non-aerosol personal skincare product. The various components of the present invention, and the manner in which they interrelate, are described in greater detail hereinafter.

The present invention comprises a number of components, each of which have their own purpose and use. Specifically, the foamed, non-aerosol personal skincare product comprises water, benzalkonium chloride, phenoxyethanol, aloe, liquid coconut, propylene glycol, collagen, polyethylene glycol, sodium benzoate, petrolatum, lanolin, mineral oil, cod liver oil, paraffin, sodium, olive oil, cottonseed oil, vitamin E, and a non-ionic copolymer such as Poloxamer 188 or a combination therefrom. Water is the solvent used for the present invention and is preferred over an alcohol-based solvent because it does not evaporate as quickly and leaves no scent or oily residue. Preferably the water is present in an amount between 75.0-95.0% by weight and more preferably between 92-94% by weight. The next ingredient is benzalkonium chloride which serves the provide the antiseptic qualities of the present invention. Preferably, the benzalkonium chloride is present in an amount between 0.12-0.14% by weight. Phenoxyethanol is used as a preservative in the present invention and is commonly present in many cosmetics and personal care products. Preferably the phenoxyethanol is present in an amount between 0.1-2.5% by weight and more preferably in an amount between 0.15-0.25% by weight.

Aloe is included in the present invention to serve as a moisturizer. Preferably, the aloe is present in an amount between 0.01-5.0% by weight and more preferably between 0.01-1.0% by weight. Liquid coconut is included in the present invention to provide fragrance to the present invention and cover over any smell or scent from the other ingredients. Preferably the liquid coconut is present in an amount between 0.1-2.5% by weight and more preferably between 1.0-2.5% by weight.

Propylene glycol is included in the present invention to serve as another solvent and allows for the dissolution of the hydrophobic ingredients into solution. Preferably the propylene glycol is present in an amount between 1.0-20.0% by weight and more preferably in an amount between 2.0-3.0% by weight. Collagen is included in the present invention to serve as a thickening agent and to create a barrier between the wound and open air because once applied to wound and the solvents evaporate, the thickening agents will remain behind to protect the skin. Preferably collagen is present in an amount between 0.1-5.0% by weight and more preferably between 1.0-3.0% by weight. The present invention also employs polyethylene glycol as another thickening agent which is preferably present in an amount between 0.1-2.5% by weight and more preferably between 2.0-2.5% by weight. Sodium benzoate is also present in the invention as a preservative. Preferably the sodium benzoate is present between 0.01-0.1% by weight and more preferably between 0.05-0.1% by weight.

The present invention is stored as a liquid and can be kept at room temperature for long periods of time. Delivery of the present invention to a user's wound or other skin issue is best done as a foam although the invention can be applied in liquid form as well and still achieve a similar result.

The present invention may also alternatively include mineral oil in an amount between 0.0-80.0% by weight to be used as a thickening agent, cod liver oil in an amount between 0.0 10.0% by weight also as a thickening agent, paraffin in an amount between 0.0-10.0% by weight as a thickening agent, sodium salts in an amount between 0.0-10.0% by weight as a preservative, olive oil in an amount between 0.0-10.0% by weight as a moisturizer, cottonseed oil in an amount between 0.0-10.0% by weight as a moisturizer, Vitamin E in an amount between 0.0 and 2.0% by weight as a moisturizer, and non-ionic copolymer such as Poloxamer 188 in an amount between 0.0-10.0% by weight as another type of thickening agent. The present invention may also include at least one antibiotic such as bacitracin zinc, neomycin sulfate, and polymyxin B. To the extent they are included, it is preferred that anywhere from 0-440 units per gram of bacitracin zinc are included, 0-3.5 milligrams of neomycin sulfate are included, and 0-5000 units per gram of polymyxin B are included. The present invention preferably has a density between 1.001-1.190 g/mL and a pH range between 5.0 and 7.0. The present disclosure includes that contained in the appended claims, as well as that of the foregoing description.

Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A foam consisting essentially of: water; benzalkonium chloride; phenoxyethanol; aloe; liquid coconut; propylene glycol; collagen; polyethylene glycol; sodium benzoate; mineral oil; cod liver oil; paraffin; sodium salts; olive oil; cottonseed oil; and vitamin E.

2. The foam of claim 1, wherein the water is present in an amount between 75.0-95.0% by weight, the benzalkonium chloride is present in an amount between 0.12-0.14% by weight, the phenoxyethanol is present in an amount between 0.1-2.5% by weight, the aloe is present in an amount between 0.01-5.0% by weight, the liquid coconut is present in an amount between 0.1-2.5% by weight, the propylene glycol is present in an amount between 1.0-20.0% by weight, the collagen is present in an amount between 0.1-5% by weight, the polyethylene glycol is present in an amount between 0.1-2.5% by weight, and the sodium benzoate is present in an amount between 0.01-0.1% by weight.

3. The foam of claim 1, wherein the foam has a pH between 5.0 and 7.0.

4. The foam of claim 1, wherein the foam has a density between 1.001 g/ml-1.190 g/mL.

\* \* \* \* \*